(12) United States Patent
Chon et al.

(10) Patent No.: US 12,419,650 B2
(45) Date of Patent: Sep. 23, 2025

(54) SURGICAL HANDPIECE HAVING MAGAZINE-TYPE ELECTRONIC COMPONENT MODULE

(71) Applicant: SCIENCEMEDIC CO,. LTD., Anyang-si (KR)

(72) Inventors: Ki Jung Chon, Anyang-si (KR); Heon Hang Lim, Gyeonggi-do (KR); Duck Jong Kim, Suwon-si (KR); Jae Hong Jeon, Incheon (KR); Ku Young Jeon, Suwon-si (KR); Jae Chul Lee, Gyeonggi-do (KR)

(73) Assignee: SCIENCEMEDIC CO, . LTD., Anyang-si (KR)

( * ) Notice: Subject to any disclaimer, the term of this patent is extended or adjusted under 35 U.S.C. 154(b) by 422 days.

(21) Appl. No.: 17/921,849

(22) PCT Filed: Aug. 30, 2021

(86) PCT No.: PCT/KR2021/011610
§ 371 (c)(1),
(2) Date: Oct. 27, 2022

(87) PCT Pub. No.: WO2022/045853
PCT Pub. Date: Mar. 3, 2022

(65) Prior Publication Data
US 2023/0172618 A1    Jun. 8, 2023

(30) Foreign Application Priority Data
Aug. 31, 2020    (KR) ........................ 10-2020-0109888

(51) Int. Cl.
*A61B 17/16*    (2006.01)

(52) U.S. Cl.
CPC ...... *A61B 17/1628* (2013.01); *A61B 17/1622* (2013.01); *A61B 17/1626* (2013.01)

(58) Field of Classification Search
CPC . A61B 17/16; A61B 17/1613; A61B 17/1615; A61B 17/1617; A61B 17/162;
(Continued)

(56) References Cited

U.S. PATENT DOCUMENTS 5,207,697 A * 5/1993 Carusillo ........... A61B 17/1628
                                                          408/124
8,894,654 B2 * 11/2014 Anderson ............. B25B 21/002
                                                          173/176
(Continued)

FOREIGN PATENT DOCUMENTS

AU    2009262866 A1 *  1/2011  ......... A61B 17/1624
CA        2839458 A1 *  7/2014  ....... A61B 17/07207
(Continued)

*Primary Examiner* — Eric S Gibson
(74) *Attorney, Agent, or Firm* — Bridgeway IP Law Group, PLLC; Jihun Kim (57) ABSTRACT

A surgical handpiece comprises, in the form of a magazine, electronic components composed of a printed circuit board mounted on a hand grip part of the handpiece and various sensor modules provided on the printed circuit board, and the surgical handpiece is easy to maintain since the repair thereof is completed by replacing a magazine. The surgical handpiece comprises a pistol-shaped housing composed of the hand grip and a motor housing integrally formed on the top of the hand grip, wherein the hand grip comprises a grip body and a magazine groove which is formed inside the grip body and into which the magazine-type electronic component module is inserted and mounted.

4 Claims, 9 Drawing Sheets

(58) Field of Classification Search
CPC ............ A61B 17/1622; A61B 17/1624; A61B 17/1626; A61B 17/1628; A61B 17/1631; A61B 17/1633; A61B 17/1635; A61B 17/1637; A61B 17/164; A61B 17/1642; A61B 17/1655; A61B 17/1657; A61B 17/1659; A61B 17/1662; A61B 17/1664; A61B 17/1666; A61B 17/1668; A61B 17/1671; A61B 17/1673; A61B 17/1675; A61B 17/1677; A61B 17/1679; A61B 17/1682; A61B 17/1684; A61B 17/1686; A61B 17/1688; A61B 17/1691; A61B 17/1693; A61B 17/1695; A61B 17/1697; A61B 2017/0042; A61B 2017/0046

See application file for complete search history.

(56) References Cited

U.S. PATENT DOCUMENTS

| | | | | |
|---|---|---|---|---|
| 9,877,734 | B2* | 1/2018 | Anderson | A61B 17/1622 |
| 9,931,118 | B2* | 4/2018 | Shelton, IV | G16H 40/20 |
| 10,045,779 | B2* | 8/2018 | Savage | H01M 50/24 |
| 10,182,816 | B2* | 1/2019 | Shelton, IV | A61B 17/1155 |
| 10,265,090 | B2* | 4/2019 | Ingmanson | A61B 34/74 |
| 2006/0206100 | A1 | 9/2006 | Eskridge et al. | |
| 2014/0200561 | A1* | 7/2014 | Ingmanson | A61B 34/74 606/1 |
| 2016/0249919 | A1* | 9/2016 | Savage | H01M 10/613 227/175.1 |
| 2018/0325528 | A1* | 11/2018 | Windolf | A61B 17/1622 |
| 2020/0197027 | A1* | 6/2020 | Hershberger | A61B 17/1628 |
| 2023/0172618 | A1* | 6/2023 | Chon | A61B 17/1626 606/79 |

FOREIGN PATENT DOCUMENTS

| | | | | |
|---|---|---|---|---|
| CN | 103919585 A | * | 7/2014 | ....... A61B 17/07207 |
| CN | 107872967 A | * | 4/2018 | ........... A61B 17/068 |
| EP | 2756808 A1 | * | 7/2014 | ....... A61B 17/07207 |
| JP | 2008-537901 A | | 10/2008 | |
| JP | 2014136163 A | * | 7/2014 | ....... A61B 17/07207 |
| JP | 2016-195791 A | | 11/2016 | |
| KR | 10-2014-0133934 A | | 11/2014 | |
| KR | 10-1641928 B1 | | 7/2016 | |
| WO | WO-2016138059 A1 | * | 9/2016 | ........... A61B 17/068 |
| WO | WO-2018226945 A1 | * | 12/2018 | ........... A61B 17/068 |
| WO | WO-2022045853 A1 | * | 3/2022 | ........ A61B 17/1626 |

\* cited by examiner

SURGICAL HANDPIECE HAVING MAGAZINE-TYPE ELECTRONIC COMPONENT MODULE

TECHNICAL FIELD

The present invention relates to a handpiece for surgery, and more particularly, to a surgical handpiece having magazine-type electronic component module that are formed to a magazine-type and are easy-to-maintain because when the electronic component is out of order, it can be repaired by replacing the electronic component module.

BACKGROUND ART

Generally, an appearance of a surgical handpiece has a handgun-shaped structure, and a pneumatic motor is generally used as a driving power source of the handpiece. The handpiece has a structure in which the rotational force of the pneumatic motor is applied to a cutting tool (drill) through a gear assembly. Also, it is necessary to rotate a bur or drill mounted on the handpiece in a reverse direction by shifting the rotational direction of the pneumatic motor during surgery.

Since electronic components such as sensor modules and printed circuit boards are fixedly mounted inside the hand grip part, there is a problem in that it is difficult to repair the components on electronic components such as sensors or printed circuit boards if a repairman is not an expert. In some cases, despite the failure of the electronic component, there is a problem in that the reuse of the handpiece is difficult because the electronic component is internal.

DETAILED DESCRIPTION OF THE INVENTION

Technical Problem

The present invention is contrived to solve the above problems, and an object of the present invention is to provide a surgical handpiece having magazine-type electronic component module that is able to be replaced easily when the electronic component is failure because the electronic component consisting of a printed circuit board and various sensor modules mounted on the printed circuit board is detachable by being formed into a magazine-type module.

Solution to Problem

In order to achieve the above object, the present invention provides a surgical handpiece having a magazine-type electronic component module including a pistol-shaped housing portion comprising a hand grip and a motor housing part integrally formed on the upper portion of the hand grip, wherein the hand grip comprises a grip body and a magazine-type groove in which the electronic component module portion formed to a magazine shape is inserted and mounted inside the grip body.

In the present invention, the hand grip includes a trigger assembly comprising a trigger configured to protrude to the front and an assembly that extends inside the hand grip to communicate with the magazine-type groove for front and rear motion of the trigger, and a direction change switch to change the direction of a motor that is mounted through both sides of the hand grip and is protruded to one side, and is interlocked with a moving arm portion installed on one side of the electronic component module to change the direction of the motor.

In the present invention, the magazine-type electronic component module portion comprises: a base plate part mounted on the lower end of the hand grip including a battery part seating groove extending to the upper side formed inside the base plate part and an electrode part protruding into the battery part seating groove and connected to the battery part; a detachable switch part formed on the upper surface side of the base plate part to fix the battery part inserted into the battery part seating groove; a module body including a module housing connected to an upper end of the base plate, a printed circuit board mounted inside the module housing, and a connecting pin connected to the printed circuit board; and a moving arm portion mounted on one side of the module housing and driven in association with the direction change switch, wherein the base plate and the module housing are configured to a magazine shape.

In the present invention, the module housing includes: a lower ring-shaped guide formed on the lower side of the module housing and protruding to correspond to the shape of the inner circumferential surface of the magazine-type groove so that the electronic component module portion can be moved along the magazine-type groove; and an upper ring-shaped guide formed at a predetermined distance from the upper side of the lower ring-shaped guide and protruding to correspond to the shape of the inner circumferential surface of the magazine-shaped groove so that the electronic component module portion can be move along the magazine-shaped groove.

In the present invention, a pin joint portion which a connecting pin is inserted and connected is formed in the upper end of the magazine-type groove.

In the present invention, the printed circuit board includes: a direction control sensor module connected to a direction control sensor mounted at the rear of the moving arm portion and mounted on the printed circuit board to sense the movement of the moving arm portion; a trigger sensor module connected to the trigger assembly to sense the movement of the trigger and adjust the speed of the motor; a controller to change the rotating direction of the motor by analyzing the transmission signal of the sensor according to the operation of the direction change switch, to adjust the speed of the motor according to the operation of the trigger, and to display the forward/reverse direction according to the operation of the direction change switch, and to control the color of the indicator light installed on the rear surface of the motor housing; and a motor drive for driving the motor.

Effect of the Invention

The present invention has an advantage to maintain easily and to be able to repair even for unskilled people since the electronic component module is formed in a magazine type, and the repair is completed only by replacing the electronic component module when a sensor or a printed circuit board failure occurs.

In addition, the present invention has an advantage that identifies the failed component easily, since when the handpiece fails and replaces the electronic component module, if the handpiece does not operate continuously, it is easy to know the failure of the motor rather than that of the electronic component module.

MODE FOR INVENTION

Hereinafter, the present invention will be described with reference to the accompanying drawings with respect to the surgical handpiece having a magazine-type electronic component module.

Figure 1:
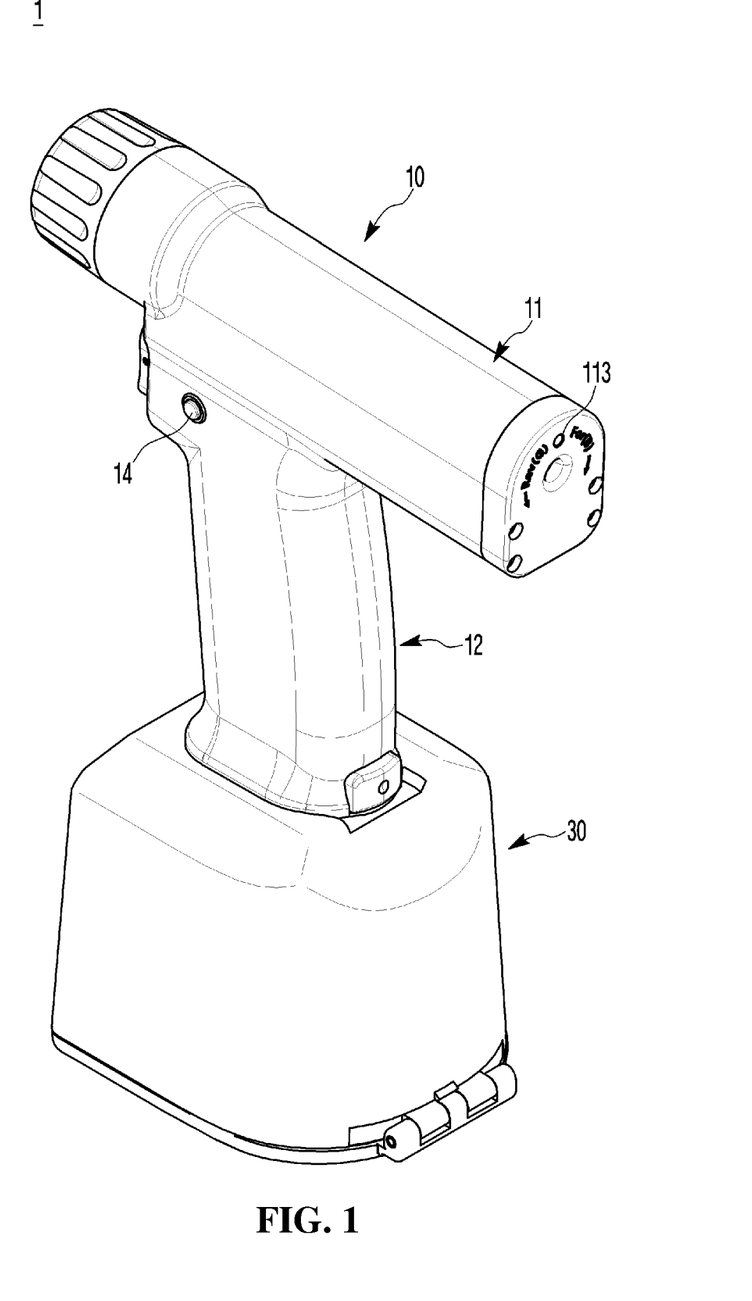
FIG. 1 is a perspective view of a surgical handpiece according to a preferred embodiment of the present invention.
Figure 2:
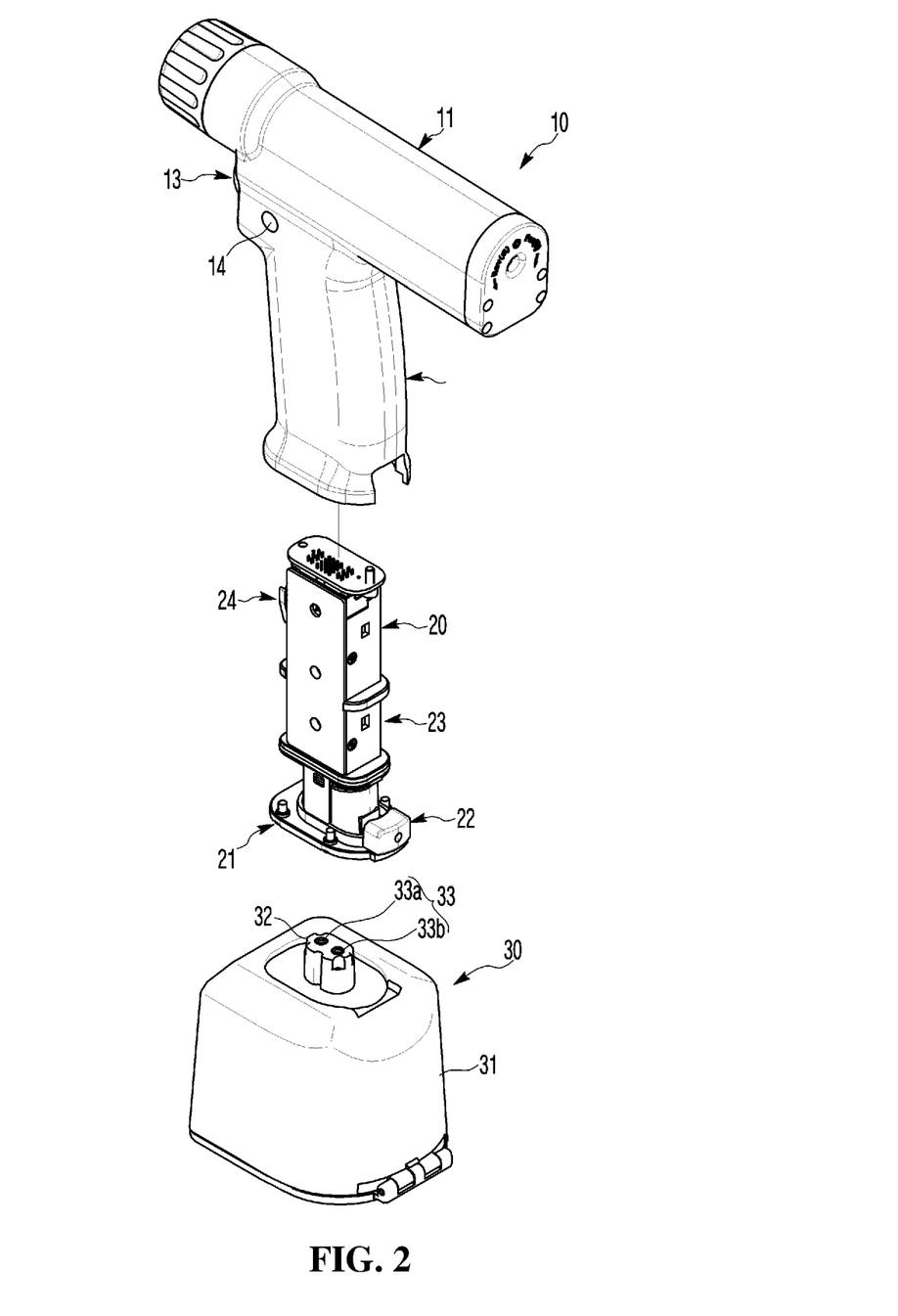
FIG. 2 is a disassembled perspective view of a surgical handpiece according to a preferred embodiment of the present invention.
Figure 3:
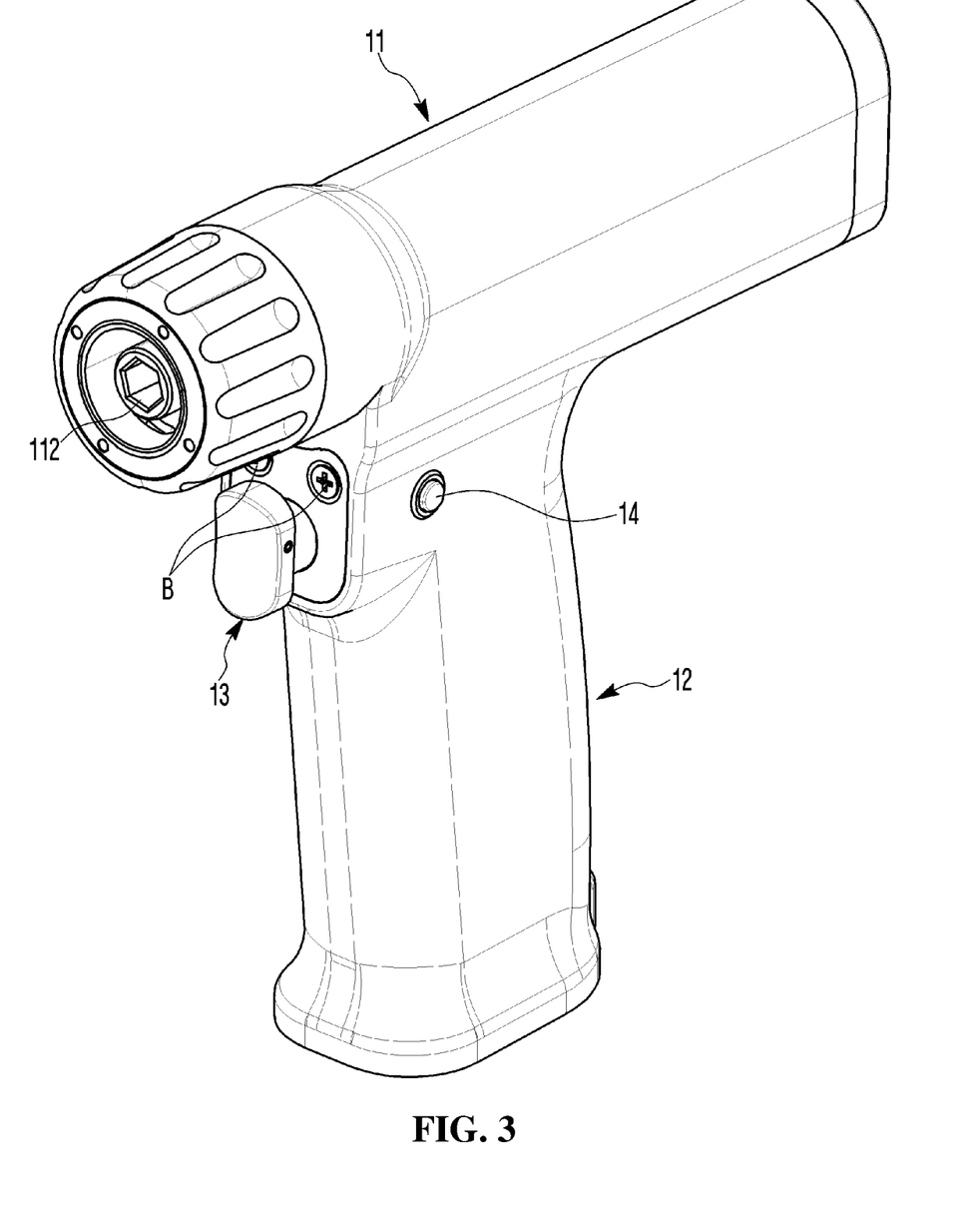
FIG. 3 is a perspective view of a state in which the battery part of a surgical handpiece is removed according to a preferred embodiment of the present invention.
Figure 4:
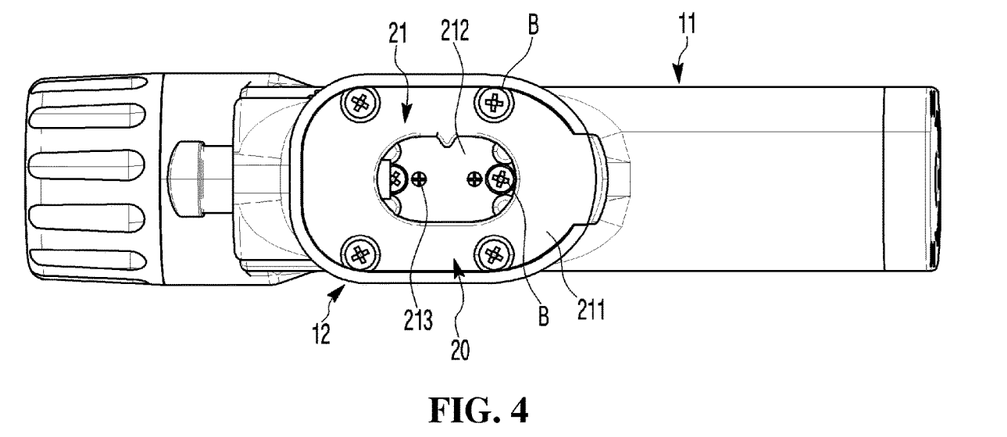
FIG. 4 is a bottom view of the handpiece of FIG. 3.
Figure 5:
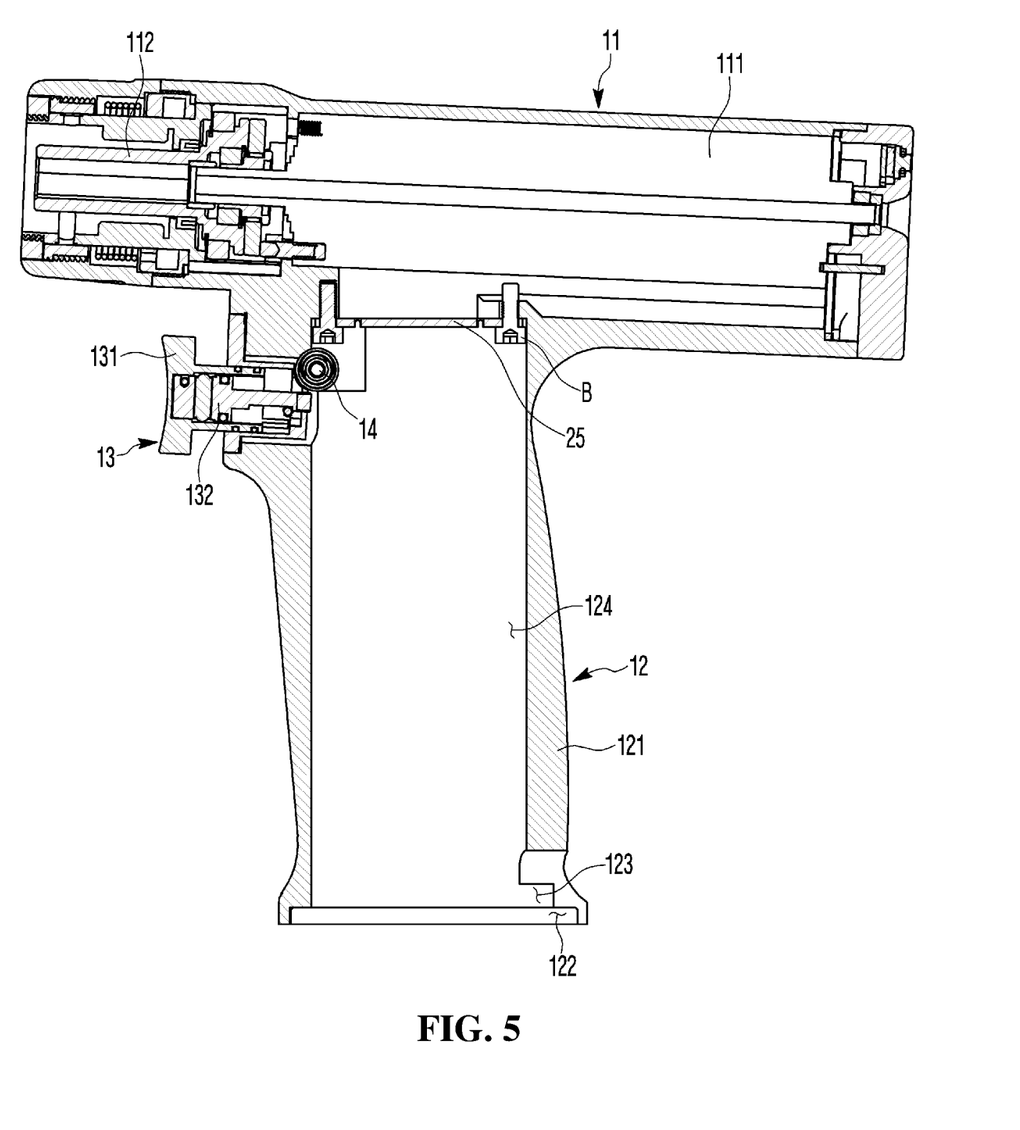
FIG. 5 is a cross-sectional view of a state in which the electronic component module is removed from the surgical handpiece according to the preferred embodiment of the present invention.
Figure 6:
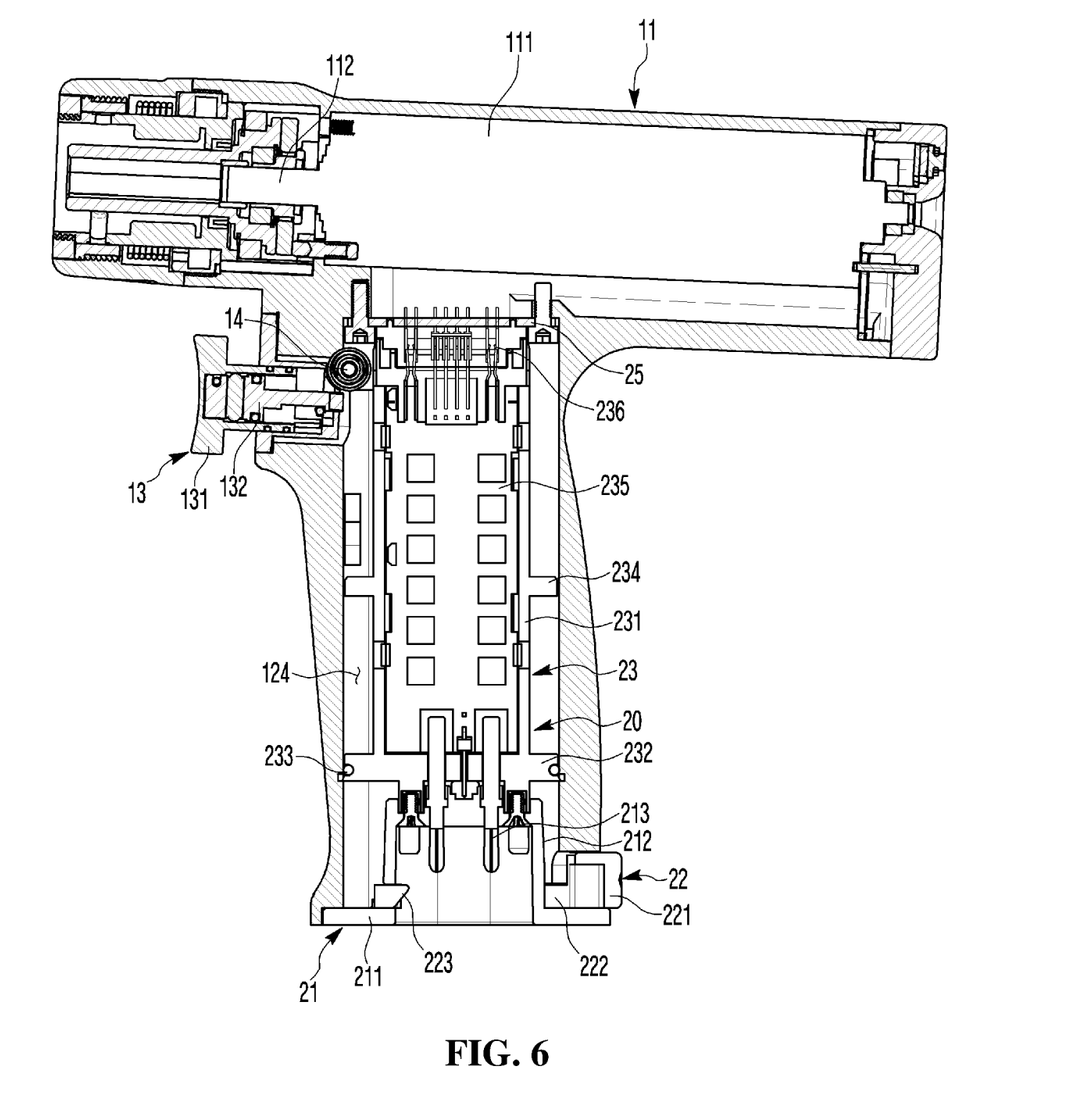
FIG. 6 is a cross-sectional view of the state including the electronic component module in the surgical handpiece according to a preferred embodiment of the present invention.
Figure 7:
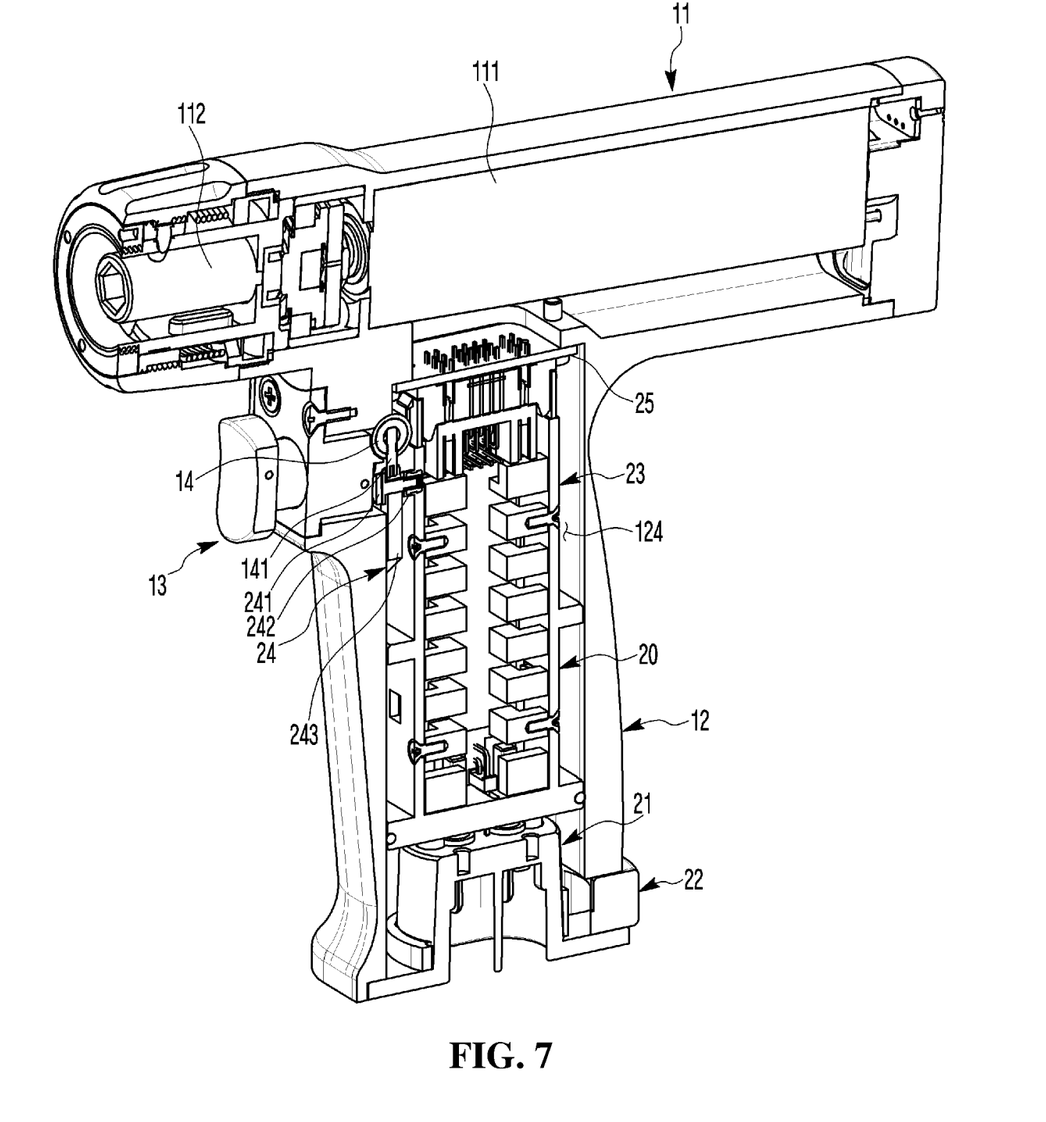
FIG. 7 is a cross-sectional view of a state in which an electronic component module is included and a direction change switch is shown in the surgical handpiece according to a preferred embodiment of the present invention.
Figure 8:
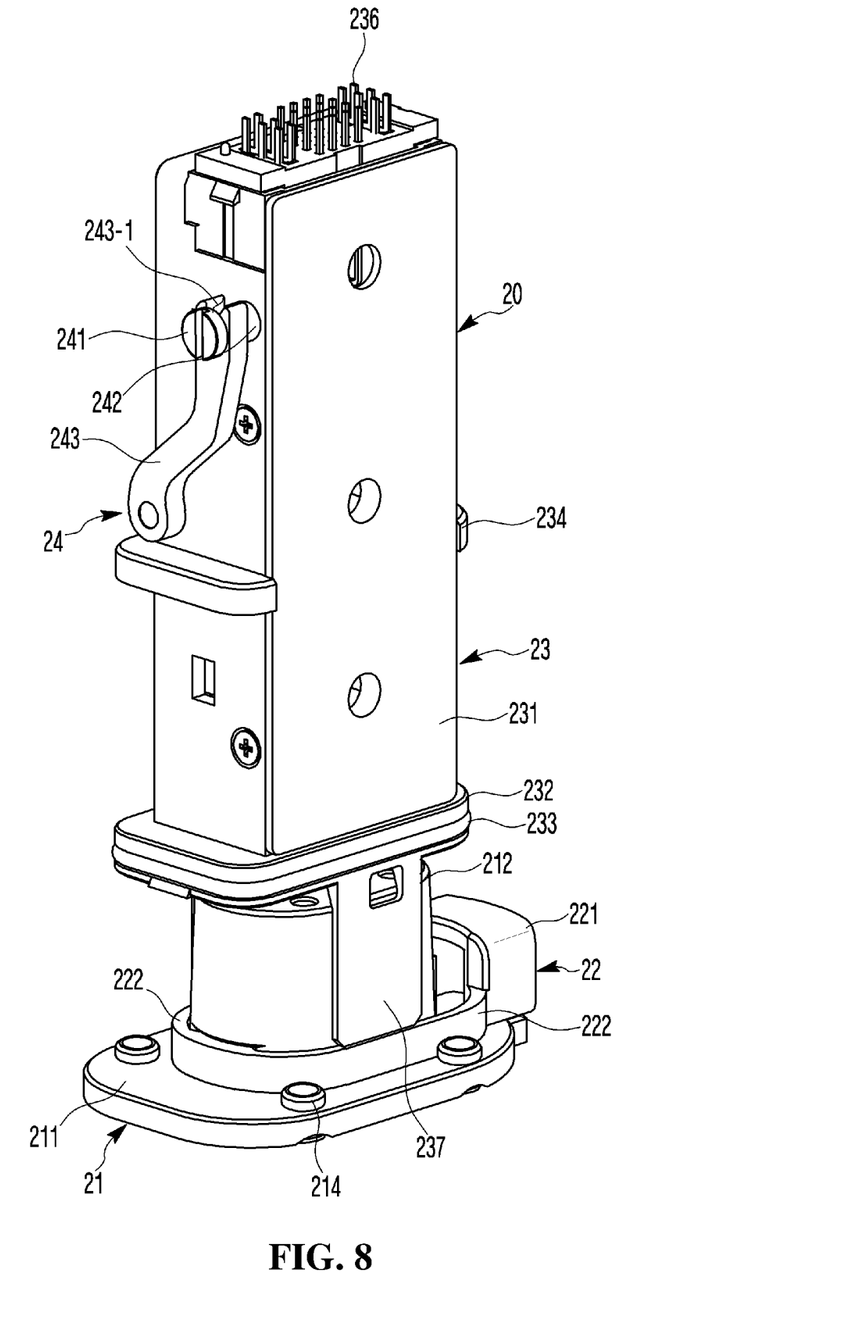
FIG. 8 and FIG. 9 are perspective views of an electronic component module in a surgical handpiece according to a preferred embodiment of the present invention.
Figure 9:
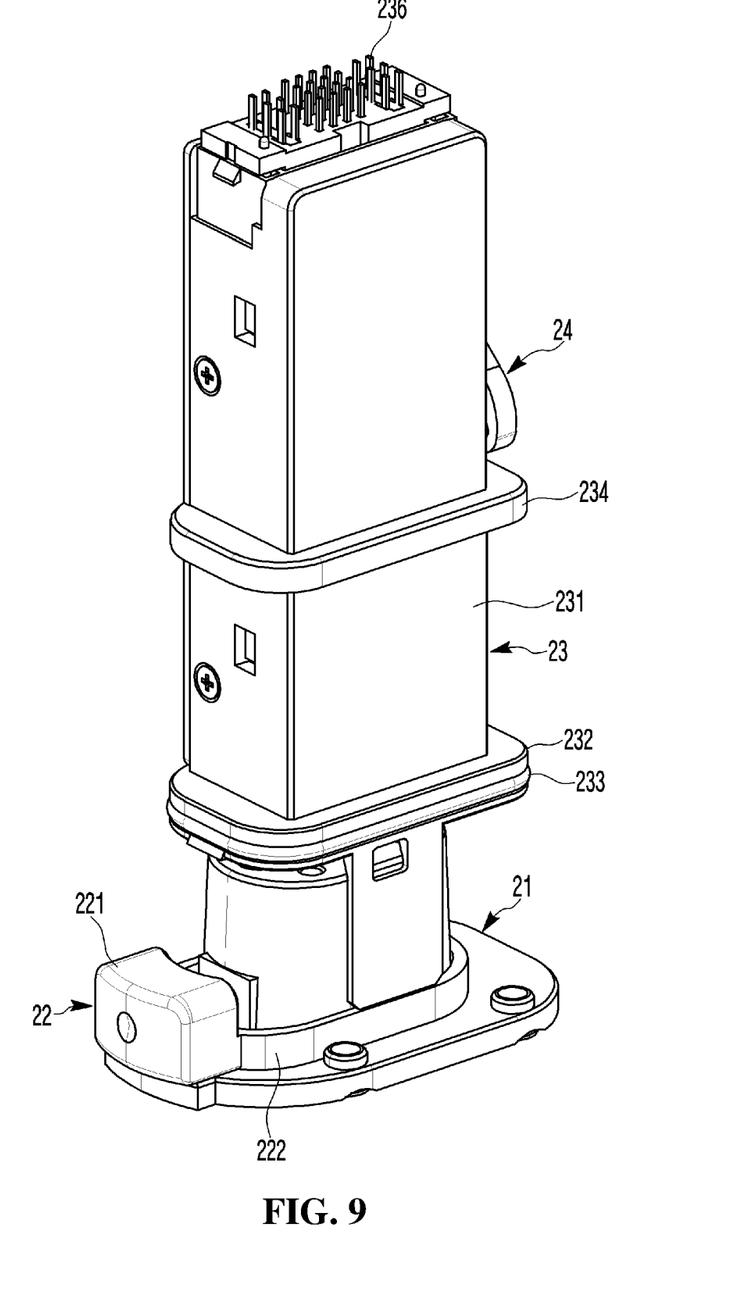

FIG. 1 is a perspective view of a surgical handpiece according to a preferred embodiment of the present invention, and FIG. 2 is a disassembled perspective view of a surgical handpiece according to a preferred embodiment of the present invention, and FIG. 3 is a perspective view of a state in which the battery part of a surgical handpiece is removed according to a preferred embodiment of the present invention, and FIG. 4 is a bottom view of the handpiece of FIG. 3, and FIG. 5 is a cross-sectional view of a state in which the electronic component module is removed from the surgical handpiece according to the preferred embodiment of the present invention, and FIG. 6 is a cross-sectional view of the state including the electronic component module in the surgical handpiece according to a preferred embodiment of the present invention, and FIG. 7 is a cross-sectional view of a state in which an electronic component module is included and a direction change switch is shown in the surgical handpiece according to a preferred embodiment of the present invention, and FIG. 8 and FIG. 9 are perspective views of an electronic component module in a surgical handpiece according to a preferred embodiment of the present invention.

FIG. 1 is a perspective view of a surgical handpiece according to a preferred embodiment of the present invention. As shown in the drawings, the handpiece 1 of the present invention is composed of a housing portion 10, an electronic component module portion 20, and a battery portion 30. The housing portion 10 includes a motor housing part 11 to which the motor 111 is mounted, a hand grip 12 to which the electronic component module portion is mounted, and a trigger assembly 13 mounted to the hand grip 12 and a direction change switch 14.

FIG. 2 is a disassembled perspective view of the handpiece 1. As shown in the figure, a motor 111 is mounted on the motor housing part 11, and the motor 111 is provided with a driving shaft 112. A display unit 113 indicating the rotating direction of the motor is mounted at the rear of the motor, and the battery portion 30 is coupled to the electronic component module unit 20 by a joint 22 at the lower end of the hand grip 12. Mounting and detachment of the battery portion 30 is performed by the detachable switch 22, and when the detachable switch 22 is pressed, the hook 223 is unlocked, and the battery portion 30 is pulled out from the electronic component module unit 20. A trigger assembly 13 is provided in front of the hand grip 12 to control the speed of the motor 111 mounted on the handpiece. A direction change switch 14 is mounted on the side of the hand grip 12. The electronic component module portion 20 is formed in a magazine shape. Specifically, the electronic component module portion 20 includes a base plate part 21 in which a battery portion seating groove 212 to mount the battery portion 30 is formed, a module body 23 positioned above of base plate part 21 which the base plate portion 21 is mounted on the lower end of module body, the detachable switch part 22 formed on the upper side of the base plate portion 21 for attaching and detaching the battery part 30, the module body 23 including the module housing 231, the printed circuit board 235 and connecting pin 236, and a moving arm portion 24 mounted on one side of the module housing 231 and driven in association with the direction change switch portion 14. The battery portion 30 includes a battery body 31, a battery joint 32 formed at the upper end of the battery body 31, and the electrode insertion hole (33: 33a, 33b) in which an electrode 213 comprising a positive electrode and a negative electrode formed in the battery joint 32 is connected.

FIG. 3 is a perspective view of the housing portion 10. As shown in the drawing, the housing portion 10 includes a motor housing part 11, a hand grip 12, a trigger assembly 13, a direction change switch part 14, and a motor shaft 112.

FIG. 4 is a bottom view of the housing unit 10 viewed from the bottom. As shown in the drawing, the electronic component module portion 20 is mounted inside the hand grip 12, and the base plate part 21 which is a component of the electronic component module portion 20 is shown. The base plate part 21 comprises a base plate 211, the joint seating groove 212 and the joint seating groove 212 in which the battery joint 32 extending upwardly from the base plate 211 is inserted and fixed, and the electrodes 213 protruding from the joint seating groove 212. The base plate part 21 is fixed to the hand grip 12 using a bolt (B). In addition, the base plate part 21 is fixed to the component module body part 23 with a bolt (B).

FIG. 5 is a cross-sectional view of the housing part 10, in particular that of the hand grip 12. As shown in the figure, the hand grip 12 includes a grip body 121, a base plate groove 122 formed inside the grip body 121, and a detachable switch groove 123 formed on the upper portion of the base plate groove 122, and a module body part mounting groove 124 formed on the upper portion of the detachable switch groove 123. The trigger assembly 13 is mounted on the front side of the hand grip 12, and the trigger assembly 13 is composed of a trigger 131, a trigger shaft 132, and a spring for sending the trigger 131 to its original position. A pin connecting part 25 into which the connecting pin 236 of the module body part 23 is inserted and fixed is further mounted inside the grip body 121. The pin connecting part 25 is fixedly mounted to the hand grip 12 with a bolt (B).

FIG. 6 and FIG. 7 are cross-sectional views of the electronic component module portion 20 installed inside the hand grip 12, and FIG. 8 to FIG. 9 are perspective views of the electronic component module portion 20. The electronic component module portion 20 will be described in detail with reference to the drawings. The electronic component module portion 20 should have a shape that can be inserted into the magazine-type groove 124. Accordingly, it has a certain shape and has a configuration corresponding to the magazine-type groove 124. As explained above, the electronic component module portion 20 includes a base plate part 21, a detachable switch part 22, and a module body part 23. The base plate part 21 includes a base plate 211, a battery seating groove 212 extending from the center side of the base plate 211 to an upper side, and an electrode 213 formed in the battery seating groove 212, and a bolt hole 214 for fixing to the lower end of the hand grip 12. The detachable switch part 22 includes a detachable switch 221, the annular link 222 form to the inside of the detachable switch 221, and a hook 223 to fix the battery portion 30 which is formed to the inside of the annular link 222 on the opposite side of the detachable switch 221. The module body 23 includes a module housing 231, a printed circuit board 235 mounted to the inside of the module housing 231, and a connecting pin 236 connected to the printed circuit board 235. The module housing 231 comprises a lower ring-shaped guide protruding in a corresponding shape to be movable along inner circumferential surface of the magazine-type groove, and a upper ring-shaped guide 234 is formed with a predetermined distance on the upper side of the lower ring-shaped guide 232 protruding in a corresponding shape to be movable along the inner circumferential surface of the magazine-type groove 124. A packing groove is formed on the outer peripheral surface of the lower ring-shaped guide 232, and since the packing 233 is inserted and mounted in the packing groove, the position can be fixed in the magazine-type groove 124.

An operating relationship between the direction change switch 14 and the moving arm portion 24 will be described with reference to FIG. 7. The switch bar 141 is connected to the lower end of the direction change switch 14. The switch bar 141 moves to left or right together when the direction change switch 14 is pressed. The switch bar 141 is interlocked with the moving arm portion 24 mounted on the front side of the module housing 231. The moving arm portion 24 includes a hinge fastening groove 242, a hinge 241 fastened to the hinge fastening groove 242, and a moving arm 243 having an upper end fixed to the hinge 241. The upper end of the moving arm 243 fixed to the hinge is opened, and the switch bar 141 is inserted into the opening 243-1 so that the moving arm 243 also move together as the direction change switch 14 moves to left or right. The rotating direction of the motor 111 may be switched by a link detection sensor that detects the movement of the moving arm 243.

A direction change sensor module installed the module housing 231 of the rear side of the moving arm 243 and connected with a direction adjustment sensor (not shown) for sensing the movement of the moving arm, a trigger sensor module that is connected to a trigger sensor that senses the movement of the trigger 141 to control the speed of the motor, and a control part which analyzes transmission signal of the sensor according to the operation of the direction change switch 14 to change the rotating direction of the motor, adjusts the speed of the motor according to the operation of the trigger 141, display the forward/reverse direction according to the operation of the direction change switch 14, and controls the color of the indicator light 113 which is installed on the rear side of the motor housing are provided in the printed circuit board 235 which is a component of the electronic component module portion 20. In addition, a motor drive (not shown) for driving the motor 111 is also provided on the printed circuit board.

When describing the display part 113 shown in FIG. 1, the display part 113 is mounted on the rear side of the motor housing 11 to display the forward or reverse rotation of the motor and it is composed of the forward display part, the reverse display part and the direction indicating light. The indicating light is composed of LED lights, and in the case of the forward direction, blue (Blue: B) is turned on, and in the case of the reverse direction, green (Green: G) is turned on the display part. Accordingly, the user can easily know the rotation direction of the motor according to the color of the indicating light.

In the handpiece 1 according to the present invention, the electronic component module portion 20 is inserted and mounted in the magazine-type groove 124 formed in the hand grip 12, and in case of failure, electronic component module portion has the advantage to maintain easily because the problem is solved as the failure one is removed and a new one is replaced. It has the advantage of being easy. In order to remove the electronic component module portion 20, the trigger assembly 13 is first removed. After removing the bolt B fixing the trigger assembly 13 and removing the hinge 241 and the moving arm 243 of the moving arm portion 24, the electronic component module portion 20 is removed. Replacing it and installing it is the reverse process.

Therefore, since the handpiece 1 according to the present invention is easy to replace the electronic component module portion 20, there is an advantage that even a non-skilled person can easily replace it.

As described above, the present invention has been described in detail with reference to preferred embodiments, but the present invention is not limited to the above-described embodiments, and various modifications are made within the scope of the claims, the detailed description of the invention, and the accompanying drawings, and these modifications also belongs to the present invention.

The invention claimed is:

1. A surgical handpiece having a magazine-type electronic component module including a pistol-shaped housing portion, the surgical handpiece comprising:
   a hand grip; and
   a motor housing part integrally disposed on an upper portion of the hand grip,
   wherein the hand grip comprises a grip body and a magazine-type groove in which the magazine-type electronic component module is inserted and disposed inside the grip body,
   wherein the hand grip includes a trigger assembly comprising a trigger configured to protrude forward, an assembly that extends inside the hand grip to communicate with the magazine-type groove for a front and rear motion of the trigger, and a direction change switch penetrating through opposite sides of the hand grip, protruding towards one of the opposite sides of the hand grip, and interlocking with a moving arm portion installed on one side of the magazine-type electronic component module to change a rotational direction of a motor,
   wherein the magazine-type electronic component module comprises:
   a base plate disposed on a bottom end of the hand grip, the base plate including a battery part seating groove extending upwardly from the base plate and an electrode part protruding into the battery part seating groove and connected to a battery part;
   a detachable switch part disposed on an upper side of the base plate to fix the battery part inserted into the battery part seating groove;
   a module body including a module housing connected to an upper end of the base plate, a printed circuit board disposed inside the module housing, and a connecting pin connected to the printed circuit board; and the moving arm portion disposed on one side of the module housing and driven in association with the direction change switch, wherein the base plate and the module housing are configured to have a magazine-type structure.

2. The surgical handpiece of claim 1, wherein the module housing includes a lower ring-shaped guide disposed on a lower side of the module housing and protruding to correspond to a shape of an inner circumferential surface of the magazine-type groove so that the magazine-type electronic component module can be moved along the magazine-type groove; and an upper ring-shaped guide disposed at a predetermined distance from an upper side of the lower ring-shaped guide and protruding to correspond to the shape of the inner circumferential surface of the magazine-type groove so that the magazine-type electronic component module can be moved along the magazine-type groove.

3. The surgical handpiece of claim 2, wherein a pin connector is disposed at an upper end of the magazine-type groove, and wherein the pin connector is configured to receive and mechanically connect to the connecting pin extending from the magazine-type electronic component module.

4. The surgical handpiece of claim 3, wherein the printed circuit board comprises:

a direction control sensor module connected to a direction control sensor disposed at a rear of the moving arm portion, the direction control sensor module being configured to detect movement of the moving arm portion;

a trigger sensor module connected to the trigger assembly and configured to detect movement of the trigger and adjust a speed of the motor;

a controller configured to change the rotational direction of the motor based on a transmission signal from the direction control sensor module, adjust the speed of the motor on the trigger sensor module to, control display of a forward or reverse direction based on an operation of the direction change switch, and control a color of an indicator light installed on a rear surface of the motor housing part; and a motor drive circuit configured to drive the motor.

* * * * *